United States Patent
Wardle

(10) Patent No.: US 6,432,039 B1
(45) Date of Patent: Aug. 13, 2002

(54) METHODS AND APPARATUS FOR REINFORCEMENT OF THE HEART VENTRICLES

(75) Inventor: John L. Wardle, San Clemente, CA (US)

(73) Assignee: Corset, Inc., Los Angeles, CA (US)

( * ) Notice: Subject to any disclaimer, the term of this patent is extended or adjusted under 35 U.S.C. 154(b) by 0 days.

(21) Appl. No.: 09/346,643

(22) Filed: Jul. 1, 1999

Related U.S. Application Data

(60) Provisional application No. 60/113,232, filed on Dec. 21, 1998.

(51) Int. Cl.[7] .................................................. A61F 13/00

(52) U.S. Cl. ........................................... 600/37; 600/16

(58) Field of Search ..................... 600/37, 18; 128/897; 623/3

(56) References Cited

U.S. PATENT DOCUMENTS

| | | | |
|---|---|---|---|
| 2,826,193 | A | 3/1958 | Vineberg |
| 3,464,322 | A | 9/1969 | Pequignot |
| 3,513,836 | A | 5/1970 | Sausse |

(List continued on next page.)

FOREIGN PATENT DOCUMENTS

| | | |
|---|---|---|
| EP | 0 370 931 | 5/1990 |
| FR | 2 645 739 A1 | 10/1990 |
| GB | 2 115 287 A | 9/1983 |
| JP | 2271829 | 11/1990 |
| SU | 1734767 A1 | 5/1992 |
| SU | 1009457 A | 4/1997 |
| WO | WO98/55165 | 10/1998 |

OTHER PUBLICATIONS

International Search Report for corresponding PCT application No. PCT/US99/30138.
"Myocardial Substitution With A Stimulated Skeletal Muscle: First Successful Clinical Case" by Carpentier et al.; *The Lancet*, Jun. 1, 1985, pp. 1267.
"Dynamic Cardiomyoplasty At Seven Years" by Carpentier et al.; *The Journal of Thoracic and Cardiovascular Surgery*, vol. 106, No. 1, pp. 42–54.
"Nonstimulated Cardiomyoplasy Wrap Attenuated The Degree Of Left Ventricular Enlargement" by Chekanov; *The Society of Thoracic Surgeons*, 1994:57 pp. 84–85.
"Girdling Effect Of Nonstimulated Cardiomyoplasty On Left Ventricular Function" by Capouya et al.; *The Society of Thoracic Surgeons*, 1993:56 pp. 867–871.
"Direct Mechanical Ventricular Actuation: A Review" *Resuscitation*, 21 (1991) pp. 7–23.
"Reverse Remodeling From Cardiomyoplasty In Human Heart Failure" by Kass et al.; Circulation, vol. 91, No. 9, May 1, 1995, pp. 2314–1318.

(List continued on next page.)

*Primary Examiner*—John P. Lacyk
(74) *Attorney, Agent, or Firm*—Stout, Uxa, Buyan & Mullins, LLP; Donald E. Stout

(57) ABSTRACT

A device for treating heart disorders, and particularly cardiomyopathy. The device is comprised of a compliant containment structure shaped in a configuration such that it surrounds and encases the heart. Within this containment structure are housed two or more inflation pockets that are fabricated from a non-elastic compliant material. These pockets are disposed on the interior surface of the containment structure and are configured to oppose and support the external wall of at least one of the ventricles of the heart. In the preferred embodiment, there are a plurality of relatively small, spaced inflation pockets disposed to act against each ventricle which is to be contained.

30 Claims, 15 Drawing Sheets

U.S. PATENT DOCUMENTS

| | | |
|---|---|---|
| 3,587,567 A | 6/1971 | Schiff |
| 3,613,672 A | 10/1971 | Schiff |
| 4,536,893 A | 8/1985 | Parravicini |
| 4,628,937 A | 12/1986 | Hess et al. |
| 4,690,134 A | 9/1987 | Snyders |
| 4,827,932 A | 5/1989 | Ideker et al. |
| 4,936,857 A | 6/1990 | Kulik |
| 4,957,477 A | 9/1990 | Lundbäck |
| 4,976,730 A | 12/1990 | Kwan-Gett |
| 5,098,369 A | 3/1992 | Heilman et al. |
| 5,112,303 A | 5/1992 | Pudenz et al. |
| 5,119,804 A | 6/1992 | Anstadt |
| 5,131,905 A | 7/1992 | Grooters |
| 5,169,381 A | 12/1992 | Snyders |
| 5,197,982 A | 3/1993 | Goldsmith, III et al. |
| 5,256,132 A * | 10/1993 | Snyders .................. 600/37 |
| 5,336,254 A | 8/1994 | Brennen et al. |
| 5,383,840 A | 1/1995 | Heilman et al. |
| 5,534,024 A | 7/1996 | Rogers et al. |
| 5,603,337 A | 2/1997 | Jarvik |
| 5,702,343 A * | 12/1997 | Alferness .................. 600/37 |
| 5,713,954 A | 2/1998 | Rosenberg et al. |
| 5,749,839 A | 5/1998 | Kovacs |
| 5,800,528 A * | 9/1998 | Lederman et al. ............ 600/37 |

OTHER PUBLICATIONS

"The "Pneumomassage" Of The Heart" by Bencini et al.; Surgery, vol. 39, No. 3, Mar., 1956, pp. 375–384.

"Pulsatile Reperfusion After Cardiac Arrest Improves Neurologic Outcome" by Anstadt et al.; Ann. Surg., Oct. 1991, vol. 214, No. 4, pp. 478–490.

"New Instrument For Prolonged Mechanical Cardiac Massage" by Anstadt et al.; *Abstracts of the 38$^{th}$ Scientific Sessions,* Sup II to Circulation, vols. XXXI and XXXII, Oct. 1965, pp. 43–44.

"The Management Of Chronic Heart Failure" by Cohn; *The New England Journal of Medicine,* Aug. 15, 1996, pp. 490–498.

"Experience: Does Practice Make Perfect?" www.ccf.org/pc/quality 08/05/98.

"Heart Failure" www.heartcenter. ccf.org/patinfo/patfuide/heartfa.html 08/05/98.

Reverse Remodeling From Cardiomyoplasty In Human Heart Failure by Kass et al.; *Circulation,* vol. 91, No. 9, May 1, 1995, pp. 2314–2318.

* cited by examiner

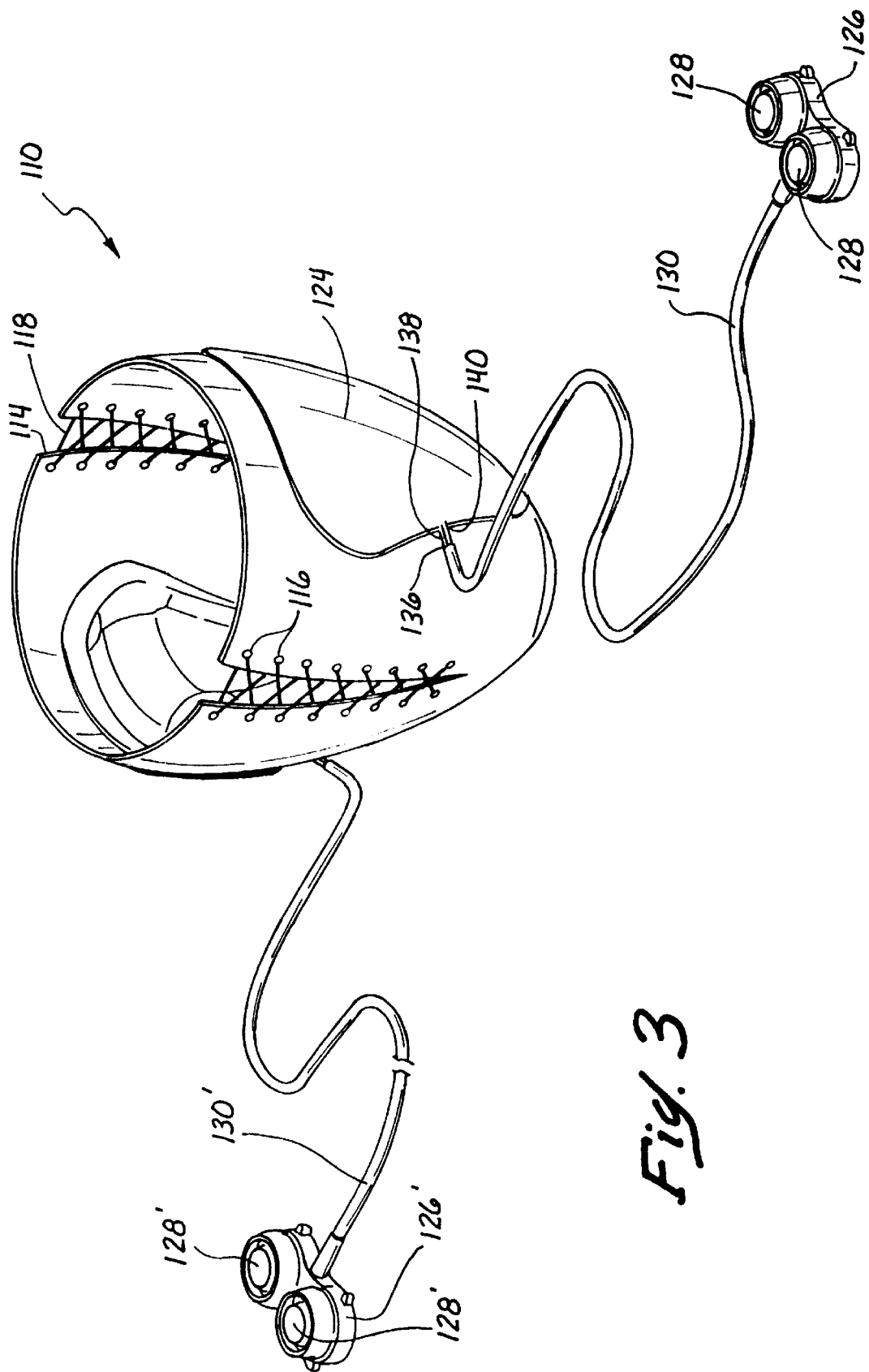

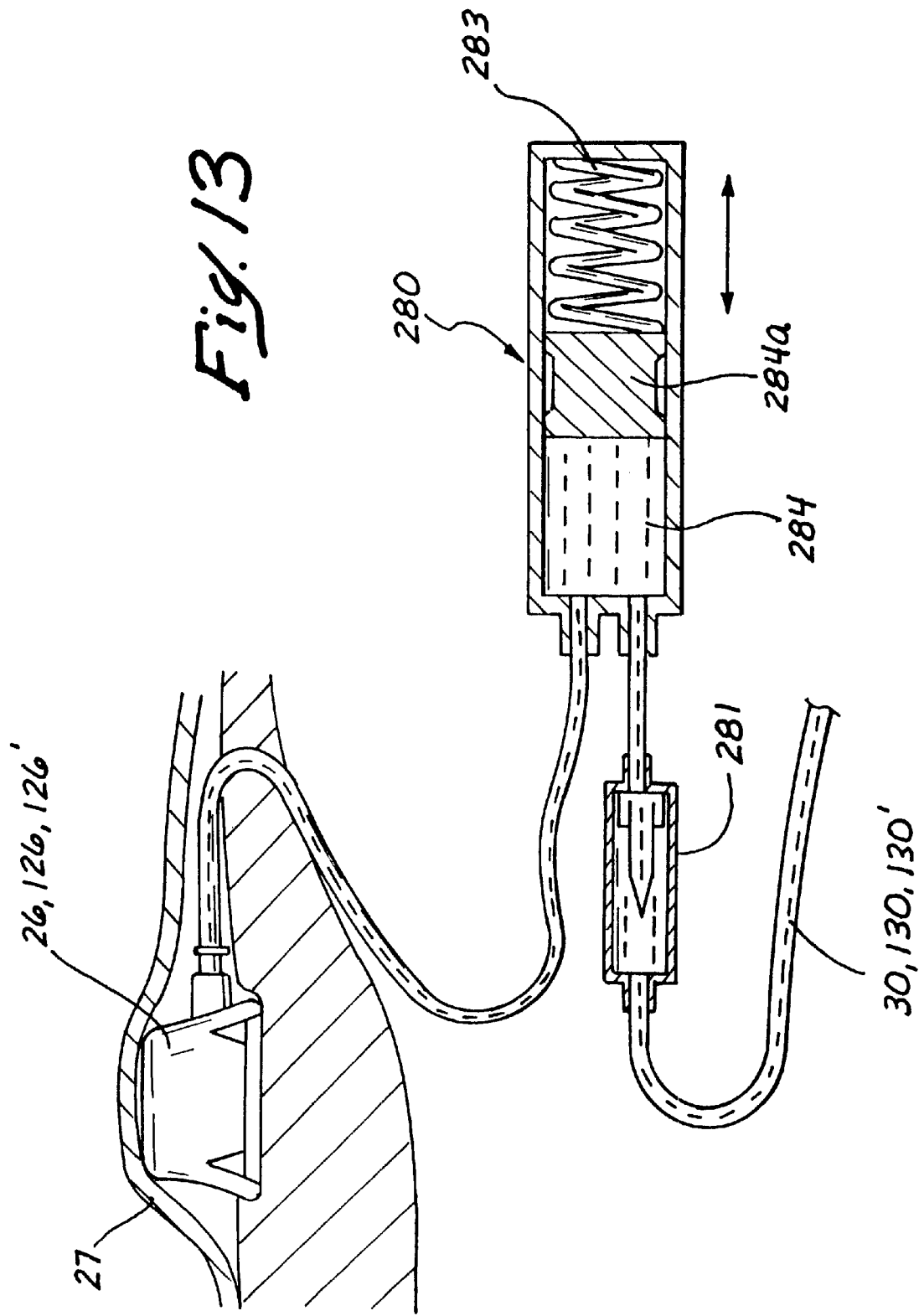

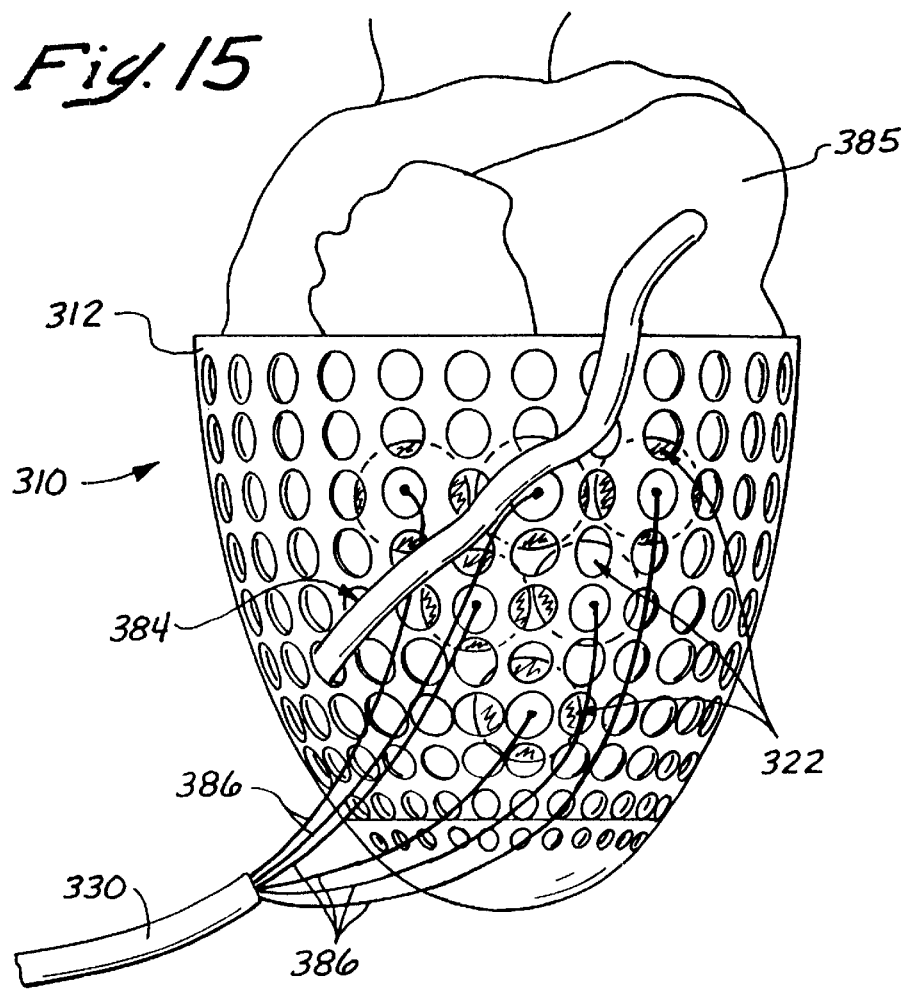
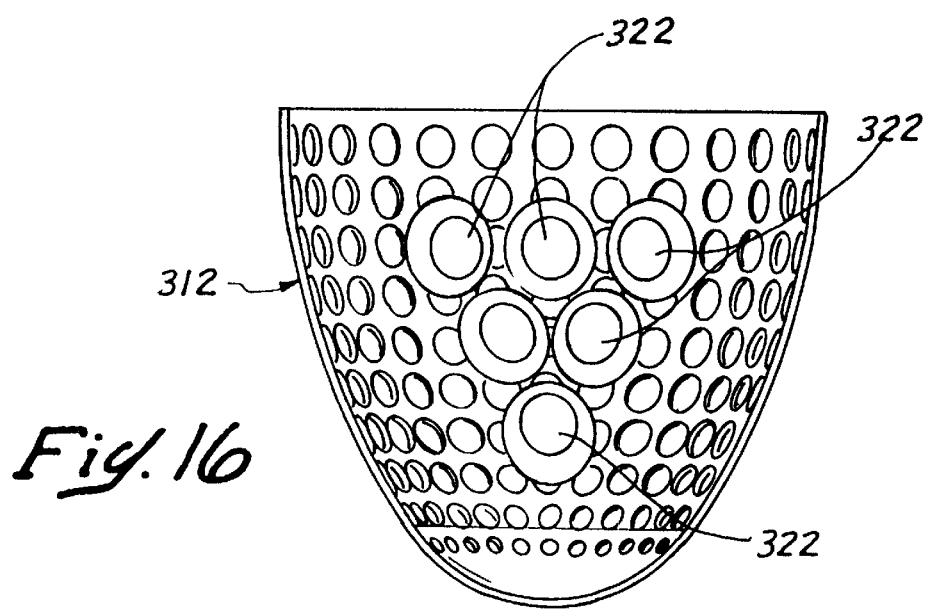

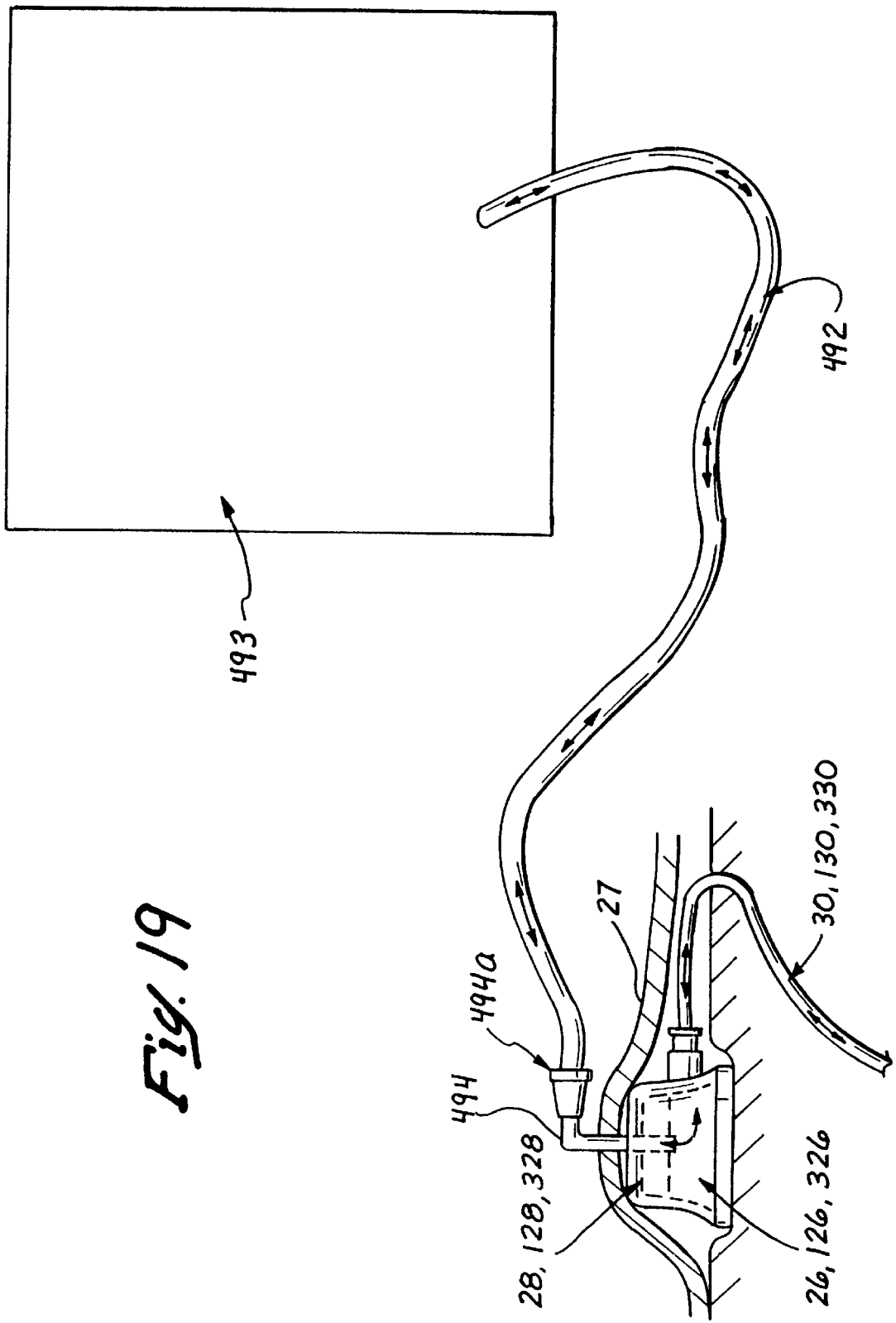

METHODS AND APPARATUS FOR REINFORCEMENT OF THE HEART VENTRICLES

This application claims the benefit of U.S. Provisional Application Serial No. 60/113,232, filed Dec. 21, 1998, which is commonly owned and the contents of which are expressly incorporated herein by reference.

FIELD OF THE INVENTION

The present invention relates to devices and methods for treating cardiomyopathy, a chronic disorder of the heart muscle, and more particularly to an implantable ventricular restraint device which is adapted to confine and control ventricular diastolic expansion.

BACKGROUND OF THE INVENTION

Cardiac dilation occurs with various diseases of the heart, including heart failure. In some instances, such as ischemic heart disease, the dilation may be localized to only a portion of the heart. On the other hand, cardiomyopathy usually results in global impairment. In the case of hypertrophic cardiomyopathy, there is typically increased resistance to filling of the left ventricle with accompanying dilation of the left atria. In dilated cardiomyopathy, the dilation is typically of the left ventricle with resultant failure of the heart as a pump. As the ventricles become enlarged, the situation is worsened by the resultant leakage which develops around the valvular structures. A sharply reduced ejection fraction is the hallmark of this condition.

Dynamic cardiomyoplasty is one treatment currently being used to treat cardiomyopathy. One current approach being used to treat this disorder is a procedure that involves wrapping and attaching a portion of a patient's own latisimus dorsi muscle around the heart, as described, for example, in the article *Reverse Remodeling from Cardiomyoplasty in Human Heart Failure*, Circulation, May 1, 1995, Vol. 91, No. 9 (Kass et al.). A pacemaker-like electrical stimulator is then attached to both the heart and the wrapped muscle. After a healing period, the wrapped muscle is electrically stimulated in synchrony with the heart which causes the muscle to contract at the appropriate time. This action actively squeezes the ventricles of the heart, to augment their function. A reversal of the heart's chronic dilated condition has been found to result in many cases, and current medical opinion is that patients with chronic heart failure may be cured of symptoms by providing assistance to ventricular function using this or similar methods. Some have also considered the benefits of merely wrapping or constraining the heart with skeletal muscle without providing active systolic assist. In any event, it will be appreciated that, although this method of treatment has proven effective, it is an open surgical procedure, which involves both removal of the patient's latisimus dorsi muscle and reattachment of the same to the heart. The frequency of the electrical stimulation, if employed, is the only adjustment that a medical professional can make to optimize the treatment for individual patients using this technique.

Another approach which has been considered to address this disorder is disclosed in U.S. Pat. No. 5,702,343 to Alferness. This patent discloses a device comprising a jacket of biocompatible material, which is applied to and adjusted to fit the epicardial surface of the heart. The device, once placed, controls cardiac expansion to a predetermined size. In one embodiment, an inflatable member is provided which is mounted between the jacket and the epicardium for selectively adjusting the size of the jacket as the heart remodels and reduces in size responsive to treatment, but there is no disclosed or suggested provision for regulating the size of the device without surgical intervention. In many cases, by the time it becomes evident that the patient is in need of treatment for cardiomyopathy, the dilation has already occurred and the patient is in chronic disorder. If the constraining device cannot be effectively and easily resized as the heart begins to remodel, it may not continue to be effective, and the possibility for a maximum remodeling of the heart may be reduced. Another drawback to the disclosed approach of Alferness is that the disclosed device applies a uniform force to both right and left ventricles. Typically, the left ventricle is the one that causes the disorder as it operates at much higher pressures. This design does not provide the medical professional with any means to accurately optimize or monitor the device's therapeutic effect. The optimal operating parameters for the device may vary dramatically from patient to patient, and these parameters can again change over time as the patient's heart becomes accustomed to the device or goes through a remodeling phase. There is typically a very small imbalance in operating forces that causes the problem and therefore a very small force is sometimes all that is required to correct the condition. Consequently, in the event that the patient were to have an adverse reaction to the device's preset configuration, an urgent surgical intervention would need to be performed to remedy the problem.

What is needed, therefore, is an improved ventricular reinforcement device which may be conveniently re-sized without surgical intervention as the heart remodels to its normal size, and which is capable of independently applying selectively differing forces against the right and left ventricles of the diseased heart.

SUMMARY OF THE INVENTION

The present invention addresses the problems outlined above by providing a unique device for treating heart disorders, and particularly cardiomyopathy, comprised of a compliant containment structure shaped in a configuration such that it surrounds and encases the heart. Within this containment structure are housed two or more inflation pockets that are fabricated from a non-elastic compliant material. These pockets are disposed on the interior surface of the containment structure and are configured to oppose and support the external wall of at least one of the ventricles of the heart. In the preferred embodiment, there are a plurality of relatively small, spaced inflation pockets disposed to act against each ventricle which is to be contained.

On the external surface of the containment structure, or spaced therefrom, there is disposed a recoil balloon, which is configured from an elastomeric material. The containment structure physically separates the inflation pockets from their associated recoil balloon(s). However, a fluid flow path is provided between the pockets and their associated balloon (s). Each recoil balloon has an inflation delivery tube which is in turn fluidly connected to a fluid access port which delivers fluid to the device as needed.

The invention, together with additional features and advantages thereof, may best be understood by reference to the following description taken in conjunction with the accompanying illustrative drawing.

BRIEF DESCRIPTION OF THE DRAWING

FIG. 3 is a schematic perspective view of a second embodiment of the present invention;

FIG. 13 is a schematic view illustrating yet a third embodiment of the inventive device;

FIG. 14b is a cross-sectional view of a portion of the embodiment illustrated in FIG. 14a;

FIG. 15 is a front elevational view showing the embodiment of FIG. 14 after it has been placed about a heart, with a bypass graft in place;

FIG. 16 is a cross-sectional view of the embodiment illustrated in FIG. 14, showing in detail the inflation pockets of the invention;

FIG. 19 is a schematic view illustrating a system for monitoring pressure and/or providing counter-pulsating assist for any one of the embodiments illustrated in FIGS. 1–18.

DESCRIPTION OF THE PREFERRED EMBODIMENT

Referring now more particularly to the drawings, there is shown in FIGS. 1, 2, 5, and 6 a first embodiment of a cardiac reinforcement device 10 of the present invention which comprises a frame or containment structure 12 preferably formed of a high strength biocompatible mesh-like material, such as polyester fully or partially encased or embedded within a flexible biocompatible material such as silicon or polyurethane, preferably using an injection process. The high strength mesh serves three primary purposes. First, it provides a strong, flexible non-elastic support for the containment structure. Second, it serves as a tear-resistant material which can be sutured to the heart muscle easily. Third, it is lightweight, and provide bypass graft access, as will be described more fully hereinbelow. The advantage of silicon, in particular, is that it has a long history of biocompatibility and provides a good surface to which other items may be attached. Of course, other suitable biocompatible materials, such as polyurethane, may be selected as well, as long as the resultant structure is compliant, but not elastic. It is also within the scope of the invention to employ an alternative configuration involving a polymer frame construction as opposed to the described mesh construction.

Figure 1:
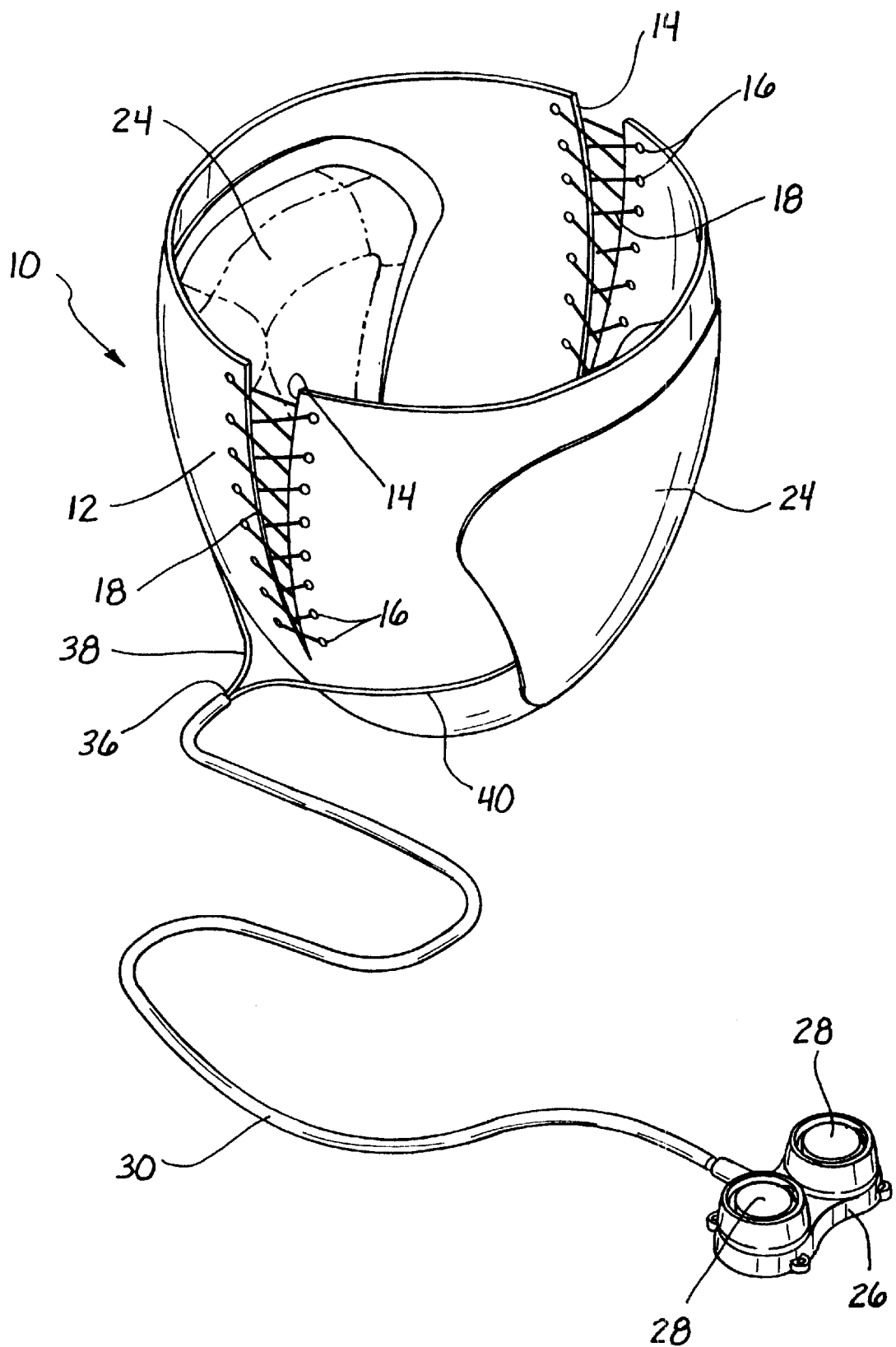
FIG. 1 is a schematic, perspective view of a first embodiment of the present invention.

The encasing elastomer for the frame or containment structure 12 may be transparent so that a practitioner can see and avoid suturing the device 10 too close to blood vessels. In this first embodiment, the containment structure 12 includes one or more slits 14 along which a series of holes 16 may be provided. Using a biocompatible lace 18, such as polyester, the slits may be laced up as illustrated in FIG. 1, for example, to optimize the size of the frame 12 for variously sized hearts.

It should be noted that, for example, as an alternative to lacing up the slits 14, VELCRO hook and loop fastening straps 18a, 18b may be provided along each side of the slit. This alternative is illustrated in FIG. 2a. During the placement of the device, the VELCRO straps 18a are overlapped to provide an accurate fit, then sutures 19 are made through the VELCRO overlap to secure the sizing permanently.

Port holes 20 are preferably provided in the frame 12 to provide a fluid flow path and permit the exchange of fluid from a plurality of inflation pockets 22 (FIG. 1) to a recoil balloon 24. The inflation pockets 22 (in this embodiment two are provided) are preferably formed of a composite structure made from a high strength biocompatible mesh-like material such as polyester fully encased within a flexible biocompatible material such as silicon or polyurethane (this may be the same material from which the frame or containment structure 12 is fabricated). These components essentially comprise balloons which are flexible and compliant with very low elasticity. Their purpose is to support the outer wall of the heart ventricle. Very low elasticity is desirable because in use there is a requirement that fluid contained within the inflation pockets 22 be expelled through the frame 12 when the pockets 22 are compressed. Consequently, a volume change due to volumetric expansion would be undesirable, as it would compromise the fit of the device on the heart. Preferably, the two provided inflation pockets 22 are of different configurations, and are asymmetrically located, due to the fact that the respective ventricles which they support are different in both configuration and location, with the left ventricle being much larger than the right ventricle. It should be noted that it is within the scope of the invention to provide more than two inflation pockets 22 if desired, since configurations wherein more than one pocket 22 supports a single ventricle may be potentially beneficial in certain instances. Such an embodiment, presently preferred, is illustrated in FIGS. 14–16.

The recoil balloon 24 is preferably fabricated of a thin high elasticity biocompatible material such as silicon or polyurethane. This component comprises a balloon which may be joined to the exterior surface of the frame or containment structure 12 over the port holes 20, as shown particularly in FIG. 2.

In the preferred embodiments, a fluid access port 26 is implanted under the patient's skin 27 (FIG. 12) for providing access through which fluid can be delivered to two different device locations. It is preferably constructed of a variety of biocompatible materials, including titanium, polysulfone, polyurethane, and silicon. Similar ports are known in the prior art for use as vascular access ports which are implanted in patients for long-term infusion of medications. The port 26 comprises a plurality of elastomeric septums 28 which can be punctured and accessed frequently with a hypodermic needle (not shown). The septum material properties are such that they self-seal upon removal of the needle.

Figure 2:
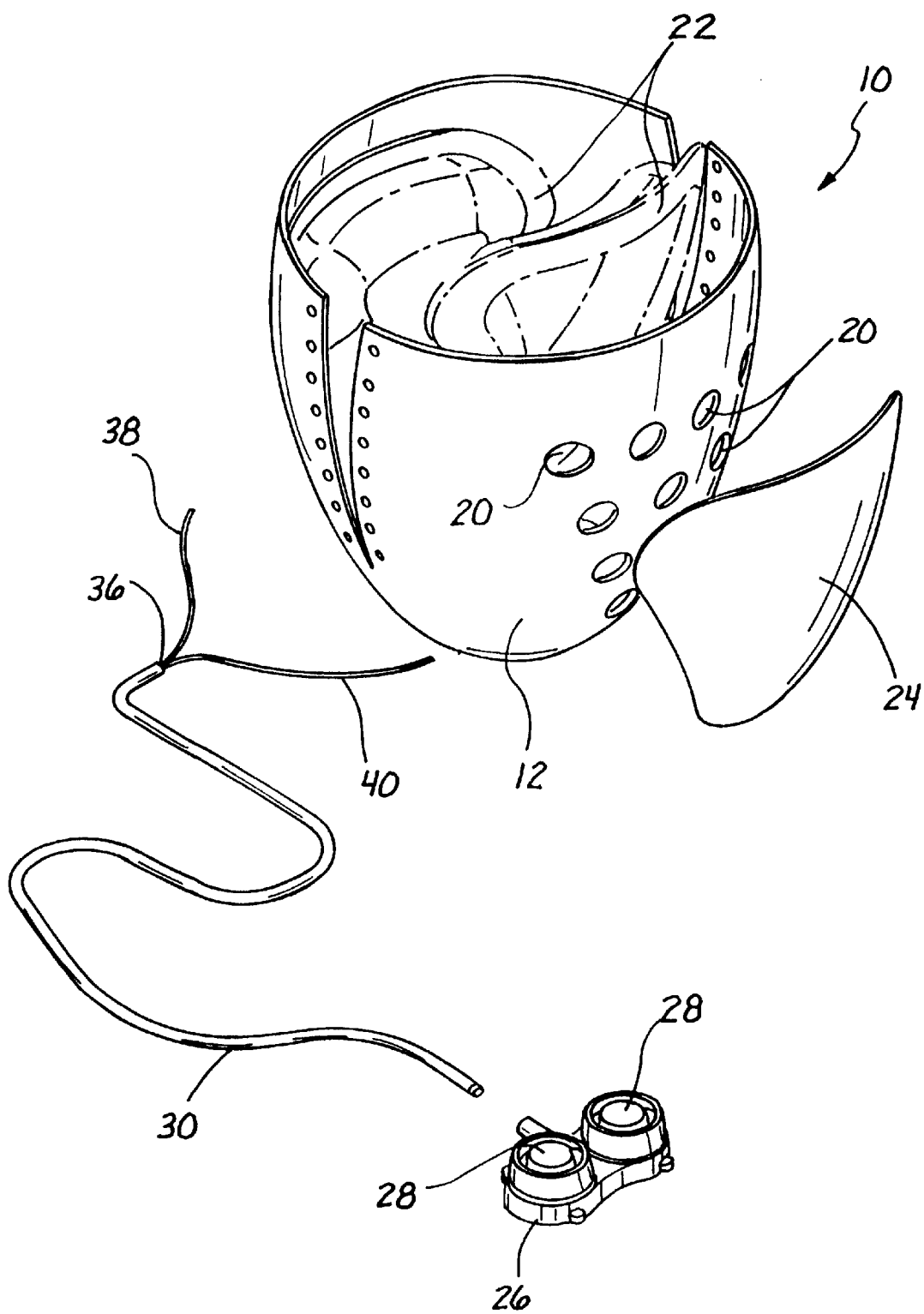
FIG. 2 is a schematic exploded view of the embodiment illustrated in FIG. 1.
Figure 2A:
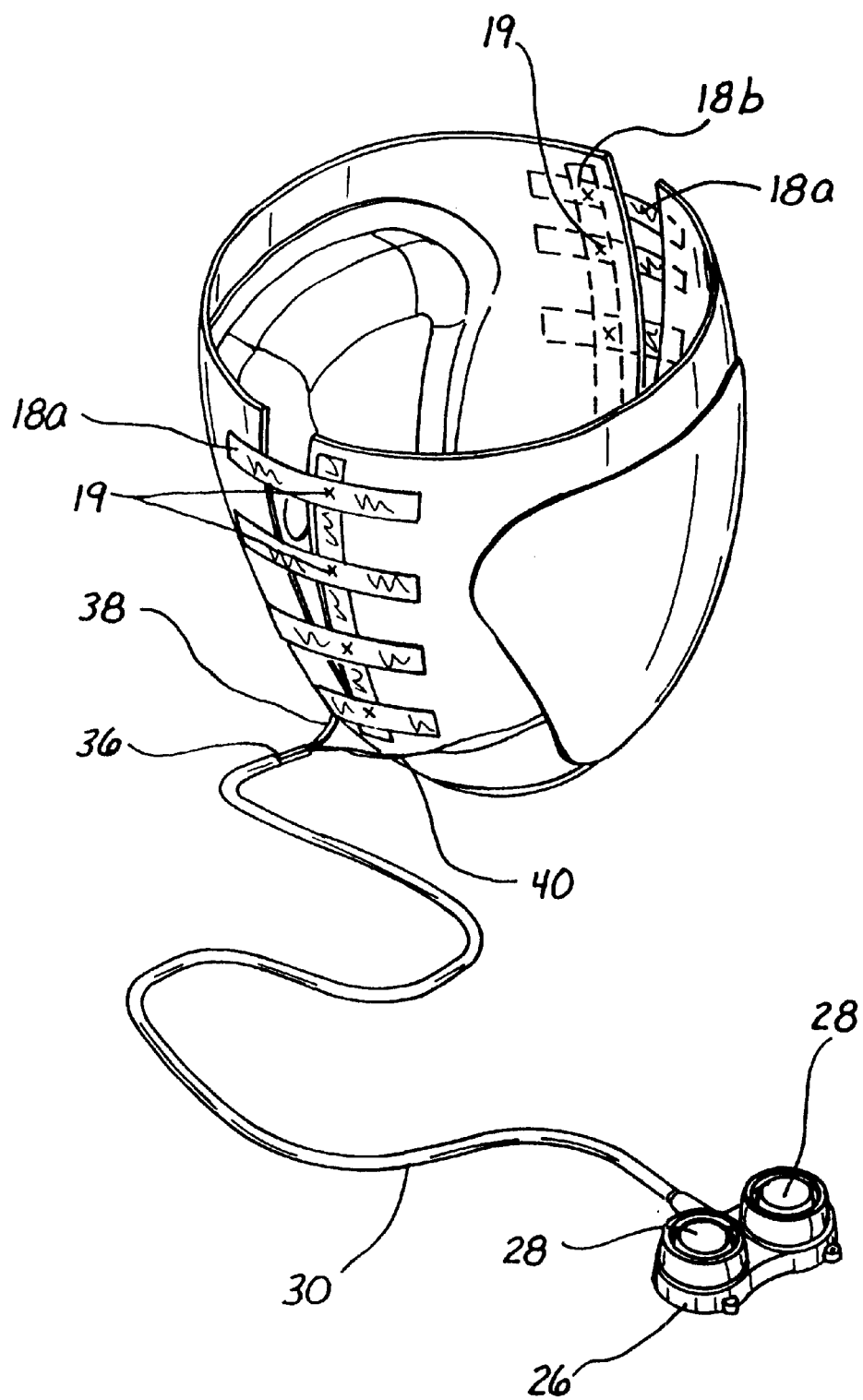
FIG. 2a is a schematic exploded view similar to that of FIG. 2, illustrating a somewhat modified version of the embodiment illustrated in FIG. 1.
Figure 4:
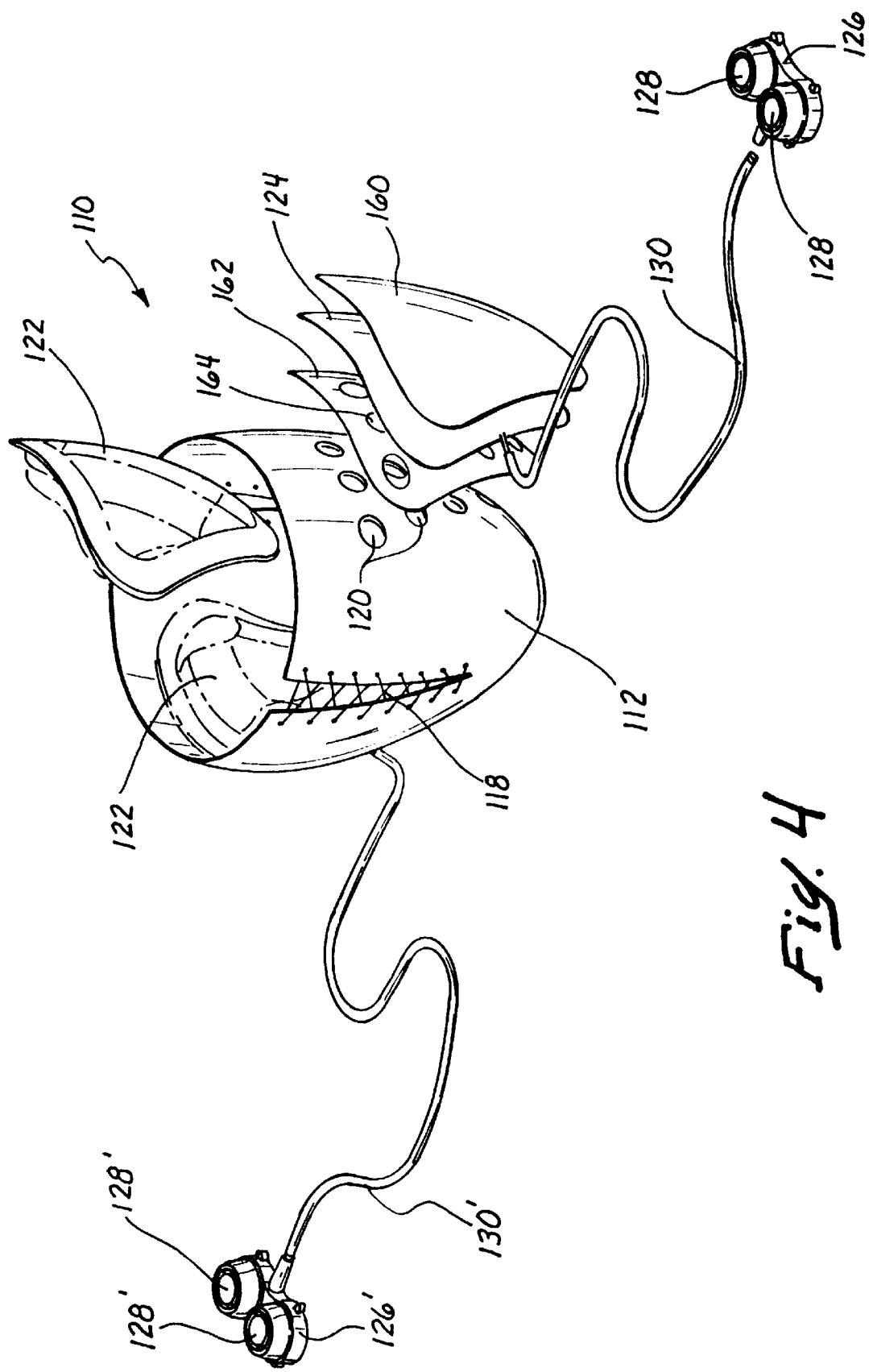
FIG. 4 is a schematic exploded view of the embodiment illustrated in FIG. 3.

A fluid line 30 conveys fluid, comprising saline or other suitable fluid, which may include both liquids and gases, from the fluid access port 26 to the recoil balloons 2 on either side of the frame 12 (only one balloon 24 is shown in FIGS. 1 and 2, but in the first embodiment there is preferably one recoil balloon associated with each inflation pocket 22). The fluid line traverses the patient's muscle 32, adjacent to the bone 34 (FIG. 12), and preferably comprises dual lumen tubing made from a biocompatible material such as silicon or polyurethane. A bifurcation 36 occurs at the distal end of the fluid line 30, and two separate tubes 38 and 40, each communicating with one of the two lumen (not shown), carry fluid to their corresponding recoil balloons. Of course, each of the lumen also corresponds to one of the two elastomeric septa 28 illustrated for this embodiment, so that the result is an ability to separately control the fluid conveyed to each recoil balloon 24.

A second embodiment is illustrated in FIGS. 3, 4, 7, and 8 (FIGS. 9–12 are common to both embodiments), wherein like elements to those in the first embodiment are denoted by like reference numerals, increased by 100. The primary difference between this embodiment and the embodiment of FIG. 1 is the provision of a second recoil balloon 160 (FIG. 4) which "piggy-backs" directly over the first recoil balloon 124. A second set of recoil balloons 160 is preferably provided on the opposing side of the frame 112 for operation with the second inflation pocket 122 (not shown). A pressure isolator plate 162, having a plurality of port holes 164, is disposed between the frame 112 and the inner recoil balloon 124. The pressure isolator plate, or recoil plate 162, is preferably made of a rigid plastic material. Additionally, a second fluid access port 126' is provided, having two septa 128' and a fluid line 130'. The fluid access port 126 is arranged to supply fluid to the two recoil balloons 124 and 160 disposed on one side of the frame 112, splitting at the bifurcation 136 (FIG. 3) so that the tube 138 from one lumen supplies the recoil balloon 124, and the tube 140 from the other lumen supplies the recoil balloon 160. Similarly, the fluid access port 126' independently supplies the two recoil balloons (not shown) disposed on the other side of the frame 112. Thus, the practitioner may independently and selectively supply differing quantities of fluid to each of the two recoil balloons disposed in a set on each side of the frame 112, and also independently supply fluid to each set of recoil balloons. In other words, all of the recoil balloons, whether in the same set or in different sets, are isolated from one another, and may be independently pressurized.

The second recoil balloon 160 may be comprised of the same material as the first recoil balloon, or it may alternatively have different material properties. A second fluid chamber 166 (FIG. 6) is provided between the first and second recoil balloons.

The pressure isolator plate, or recoil plate 162 is utilized only in the second embodiment because when the secondary recoil balloon 160 is partially inflated, it puts a compressive load on the inner recoil balloon 124, which in turn compresses the frame wall causing increased pressure on the inflation pocket 122. The purpose of the plate 162 is to isolate those forces.

In yet a third embodiment of the invention, the system may be constructed as shown in either the first or second embodiments. The only change is that, as illustrated in FIG. 13, in this embodiment the fluid access port 26, 126, 126' is augmented by a pressurized fluid reservoir system 280 having a one-way valve 281, such as a duckbill valve, for example. With this configuration, rather than manually adding fluid, fluid from the reservoir 280 may be automatically added to each of the inflation pockets 22, 122 if and when the pressure in the inflation pockets drops below a predetermined value. Preferably, in this embodiment, the fluid reservoir system 280 comprises a biasing device, such as a constant force spring 283, a fluid reservoir 284, and a seal 284a disposed between the fluid reservoir 284 and the spring 283. In operation, the spring 283 moves back as fluid enters from the fluid access port 26, 126, 126', and moves forward to push fluid out of the device. With this arrangement, the fluid reservoir pressure equals the spring force, which is always maintained as long as fluid is present.

There is shown in FIGS. 14–16 a fourth presently preferred embodiment of the invention, wherein like elements to those of the first embodiment are designated by like reference numerals, increased by 300. Elements which are the same as in prior embodiments, having similar structure and function, may not be again described. Thus, a cardiac reinforcement device 310 constructed in accordance with this embodiment comprises a containment structure 312 which is preferably fabricated entirely of a high strength biocompatible mesh-like material, such as polyester. This construction, as compared to the mesh and frame construction disclosed in connection with the prior embodiments, provides a benefit of a lighter weight structure with less bulk, and therefore greater compliance, which minimizes the impairment of cardiac function. It also improves visibility, and provides ready access for a bypass graft, as will be discussed infra. As in the prior embodiments, there are provided a plurality of port holes 320 in the structure 312, but they are preferably greater in number and distributed about the entire circumference of the structure 312, as illustrated.

It should be noted that the mesh construction for this preferred embodiment may be constructed with a square pattern, if desired, and could resemble a hair net in appearance.

Unlike the prior disclosed embodiments, this embodiment is particularly suited to the accommodation of one or more existing bypass grafts 384 (FIG. 15) which may be present on the patient's heart 385. A device constructed as illustrated in the first three embodiments may not be as suited to this type of condition, because the inflation pocket may cover and compress the bypass vessel, causing a restriction in the blood flow. In addition, in severe cases of cardiomyopathy (large dilation of the heart), there may not be sufficient space for the recoil balloons to expand without being compressed against the surrounding anatomy if they are attached to the side of the inventive device, as shown in the embodiments of FIGS. 1, 2, and 3. This compression would, of course, affect the pressures at which the device operates.

In contrast, the present embodiment comprises a plurality of multiple small inflation pockets 322, rather than the fewer, larger inflation pockets disclosed in the previous embodiments. The multiple inflation pockets 322 simulate the appearance of bubble wrap, but are spaced apart enough to provide a sufficient clearance between them to accommodate an existing bypass graft 384, or to allow a subsequent bypass graft 384 to be attached. Because the inflation pockets 322 are spaced, and small, no one pocket 322 should cover and compress the bypass vessel sufficiently to cause undesirable blood flow restriction. If, however, that is the case, because of the number of inflation pockets 322, one or more of them can be removed during the installation procedure to accommodate the existing bypass graft 384.

Furthermore, this preferred embodiment overcomes the problems discussed supra, related to the unavailability of sufficient space for the recoil balloons of the prior embodiments in the event of a severely enlarged heart, by reducing the side profile and relocating the recoil balloons away to a location where space is not at a premium. The device otherwise functions in substantially the same manner as in the previous embodiments.

Preferably, when it is necessary to perform a bypass procedure subsequent to installation of the device 310, the bypass graft is routed around the exterior surface of the structure 312. The large number of access holes 320 provided in the mesh material increase the likelihood that the graft can be attached without removing the device 310. However, in the event that additional access is required, the material comprising the structure 312 is capable of being cut to provide additional access holes without compromising the mechanical integrity of the device. In some instances, it may even be preferably to provide fewer and/or smaller access holes 320, and to just be prepared to cut additional holes during a later bypass procedure, for the purpose of access. In the prior embodiments illustrated in FIGS. 1–13, if the device were already implanted and a bypass procedure became necessary, it is highly likely that the device would need to be removed in order to gain access to the artery and make the attachment of the vessel, as the site would likely be substantially covered by one of the inflation pockets. This is a difficult prospect, because of the tendency of the frame or containment structure 12, 112 to embed itself into the surrounding tissue over time. However, in the embodiment of FIGS. 14–16, even if one or more inflation pockets 322 are in the way, they can be removed to accommodate the procedure without materially affecting the overall operating effectiveness of the device.

Preferably, the multiple inflation pockets 322 associated with each ventricle are linked together, in that they are all attached to one of the septums 328 of the fluid access port 326, as illustrated in FIG. 14. The fluid line 330 attached to each of the septums 328, which is preferably of a dual lumen construction, as discussed supra in connection with the prior embodiments, includes at its distal end a plurality of smaller fluid delivery tubes 386, which are each individually fluidly connected to a separate inflation pocket 322 disposed over an associated ventricle. With this advantageous arrangement, the inventive system may be adapted to fill the inflation pockets 322 for a particular ventricle in parallel, or in series, as desired, so that the pockets 322 may be, for example, filled in series from the base to the top of the structure 312 as the associated ventricle expands in a similar manner, or, alternatively, may be filled simultaneously.

In one version of this preferred embodiment, illustrated in FIGS. 14, 15, and 16, the recoil balloons 324 are disposed in each fluid line, remote from the structure 312, rather than being attached to the exterior surface of the frame 312, as in prior embodiments. As in the prior embodiments, the balloons 324 are preferably fabricated of a thin high elasticity biocompatible material such as silicon or polyurethane. This arrangement offers the benefit of reducing the space that the device occupies immediately around the heart, and instead permits the disposition of the balloons 324 elsewhere in the chest cavity where space may not be as restricted. One other advantage of this construction is that the balloons may be changed out by utilization of only a minor surgical procedure, involving only the removal of easily detachable fittings 387 (FIG. 14), such as Luer Locks, in the event that balloons with different pressure capacity or recoil properties would be of benefit.

Figure 14B:
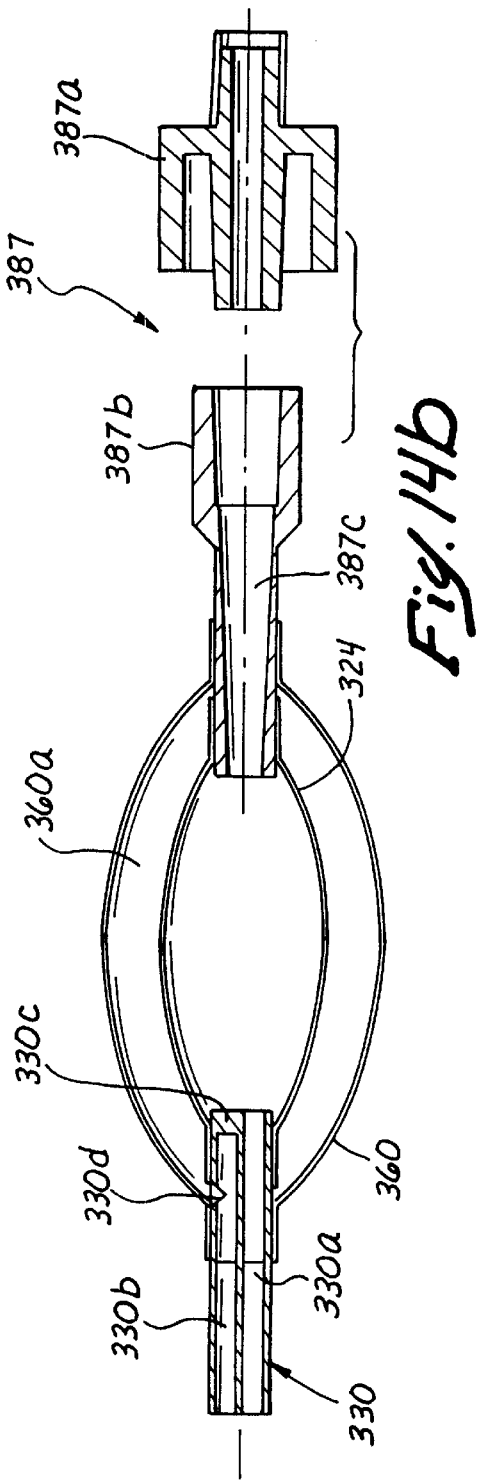
Figure 14:
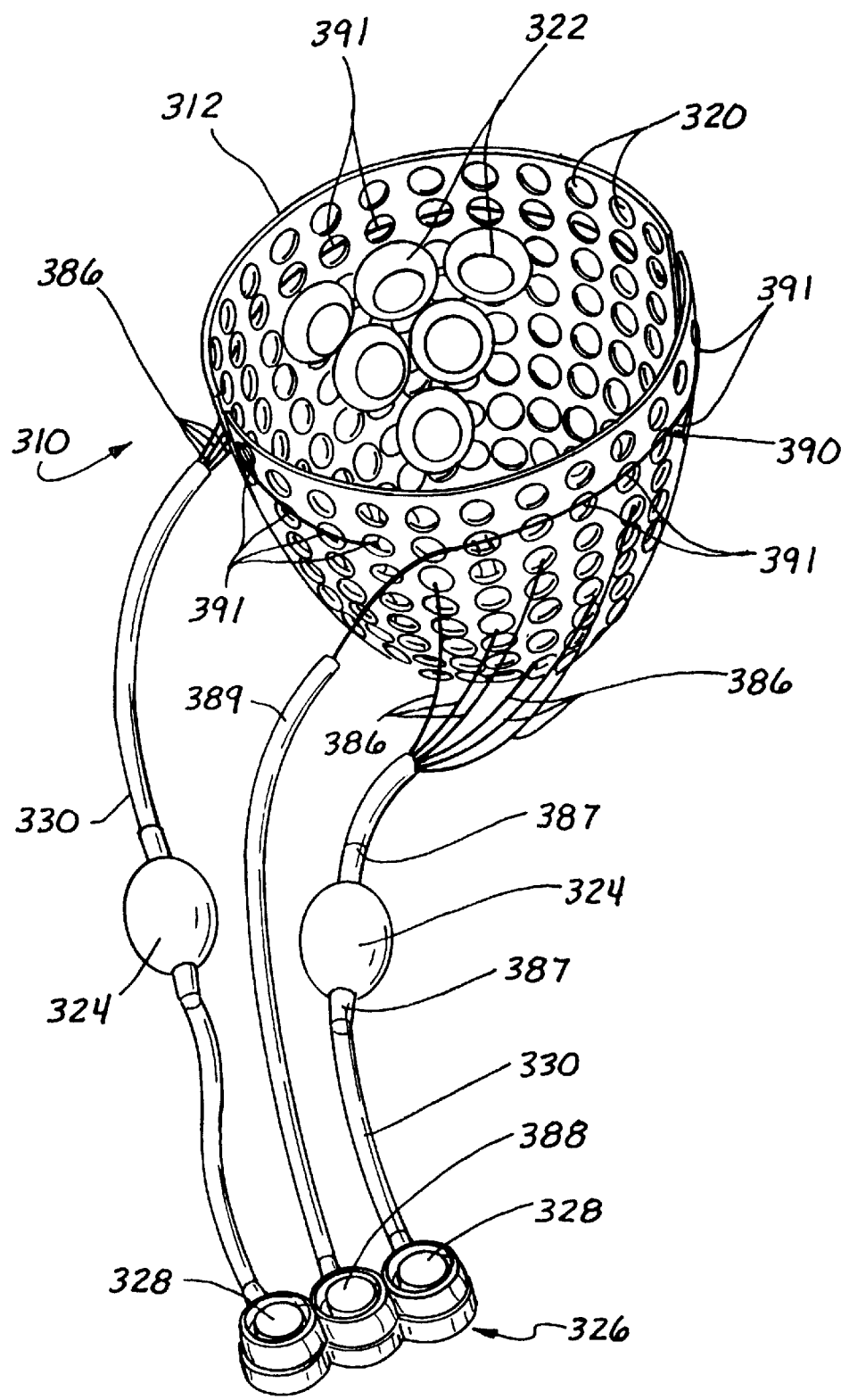
FIG. 14 is a perspective view illustrating a fourth preferred embodiment of the invention.
Figure 14A:
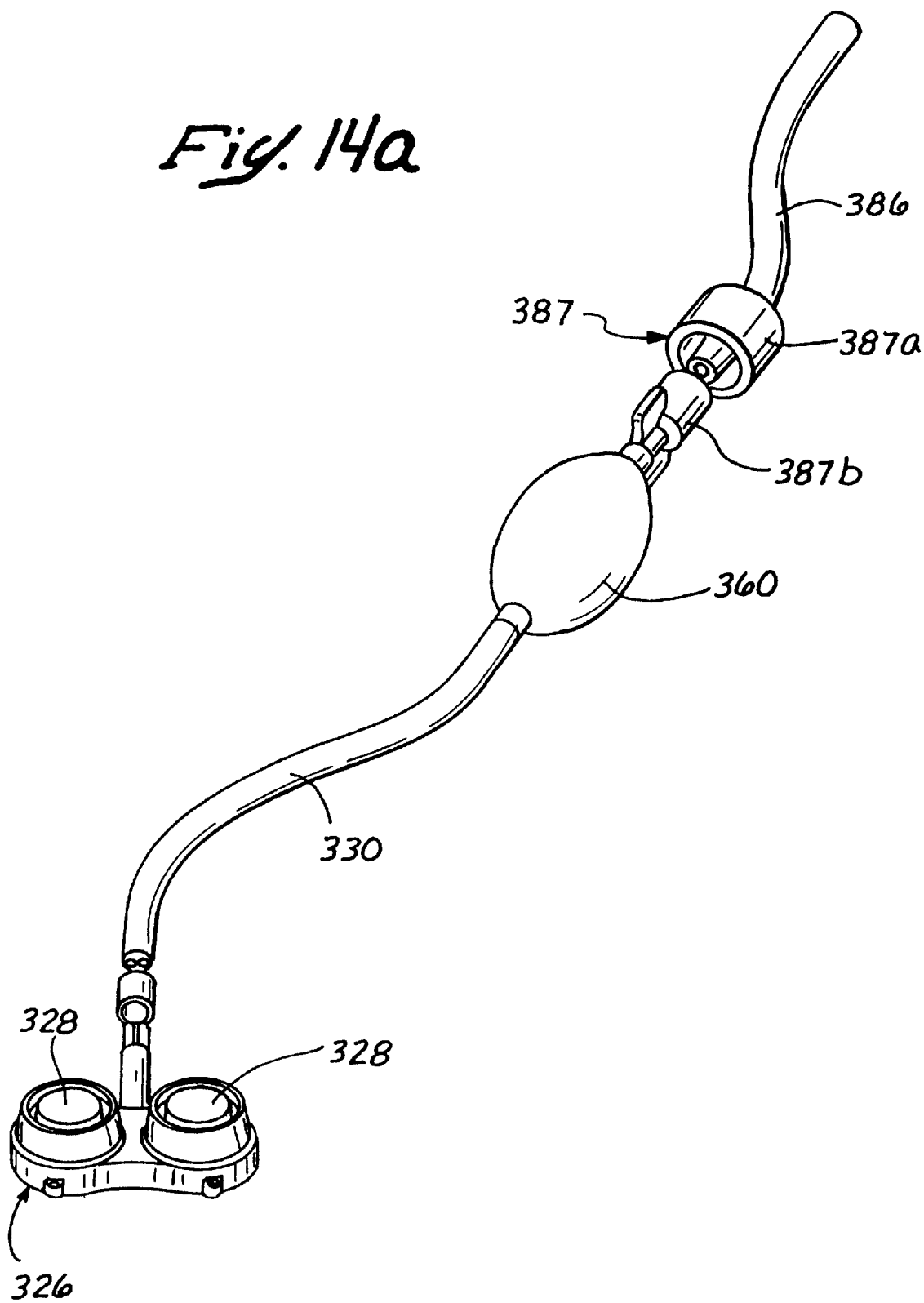
FIG. 14a is a perspective view illustrating a modified version of the fourth embodiment shown in FIG. 14.

Another version of this preferred embodiment is illustrated particularly in FIGS. 14a and 14b. This embodiment is very similar to that of FIG. 14, except that a double recoil balloon, comprised of a pair of inner and outer recoil balloons 324, 360 is utilized, rather than a single recoil balloon 324. This is similar in concept to the embodiment illustrated in FIG. 4, with back-to-back recoil balloons 124, 160. As shown, the detachable fitting 387 comprises a male Luer Lock 387a and a female Luer Lock 387b. Lumen 330a provides a fluid line for filling the inner balloon 324, while lumen 330b provides a fluid line for filling the exterior balloon 360. A fluid line block 330c forces fluid to enter the outer balloon 360 through an entry port 330d. Passage 387c in the female Luer Lock 387b provides an exit port for fluid exiting the interior recoil balloon 324 for the inflation pockets. In operation, when fluid is injected into the cavity 360a between the exterior balloon and the interior balloon, the exterior balloon 360 becomes distended and causes an increase in the filling pressure for the interior balloon 324. This configuration thus, as is apparent, provides a convenient method for increasing operating pressures, if desired, and thereby perhaps avoiding undue intervention.

Another advantageous feature of the present embodiment is its capability to directly deliver Trans echocardial drugs to the pericardium. In a preferred configuration, a third elastomeric septum 388 is provided in the fluid access port 326 (FIG. 14), which is attached to a drug delivery line 389. A distal portion 390 of the drug delivery line 389 is arranged to wrap around the exterior surface of the structure 312, as illustrated in FIG. 14, and is provided with a plurality of drug flow holes 391 spaced therealong where the distal portion 390 is in proximity to the pericardium, to ensure the uniform delivery of the drug at its intended site. The drug flow holes 391 may also be used to remove fluid from the pericardium area if this become necessary.

Figure 12:
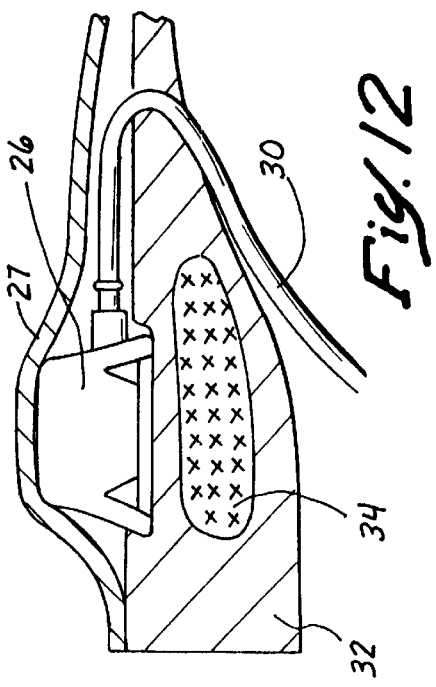
FIG. 12 is a schematic view illustrating the placement of the fluid access port which forms a part of the present invention.
Figure 11:
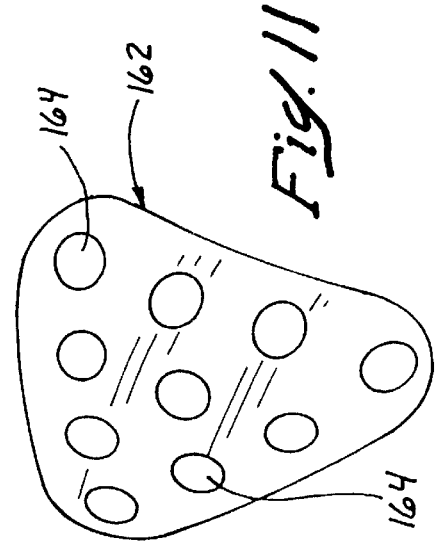
FIG. 11 is a plan view, in isolation, of the recoil plate which forms a part of the second configuration of the inventive device illustrated in FIGS. 3 and 4.

In operation, the device 10, 110, 310 is installed for operation on a patient's heart by first removing or opening up the pericardium (not shown). The frame or containment structure 12, 112, 312 is then placed over the heart with the inflation pockets 22, 122, 322 disposed adjacent to one or both of the ventricles. Using the side slits 14, 114 and laces 18, 118 which are incorporated in the frame 12, 112, or the VELCRO straps which are discussed supra at page 6, line 27 to page 7, line 4, the device can be accurately sized to the heart (the frame 312 is sufficiently elastic, being comprised entirely of flexible mesh material, that no slits are required). This is achieved in a similar manner as one would tighten a shoelace. The frame is then securely sutured to heart muscle to ensure that it cannot migrate from its intended location and also to isolate the forces on the right and left sides of the device during use. The fluid access ports 26, 126, 126', 326 are then attached to the chest just under the patient's skin 27, as illustrated in FIG. 12. Alternatively, with respect to the third embodiment shown in FIG. 13, the pressurized fluid reservoir 280 and one-way valve 282 are appropriately positioned within the patient's thoracic cavity (not shown).

Figure 5:
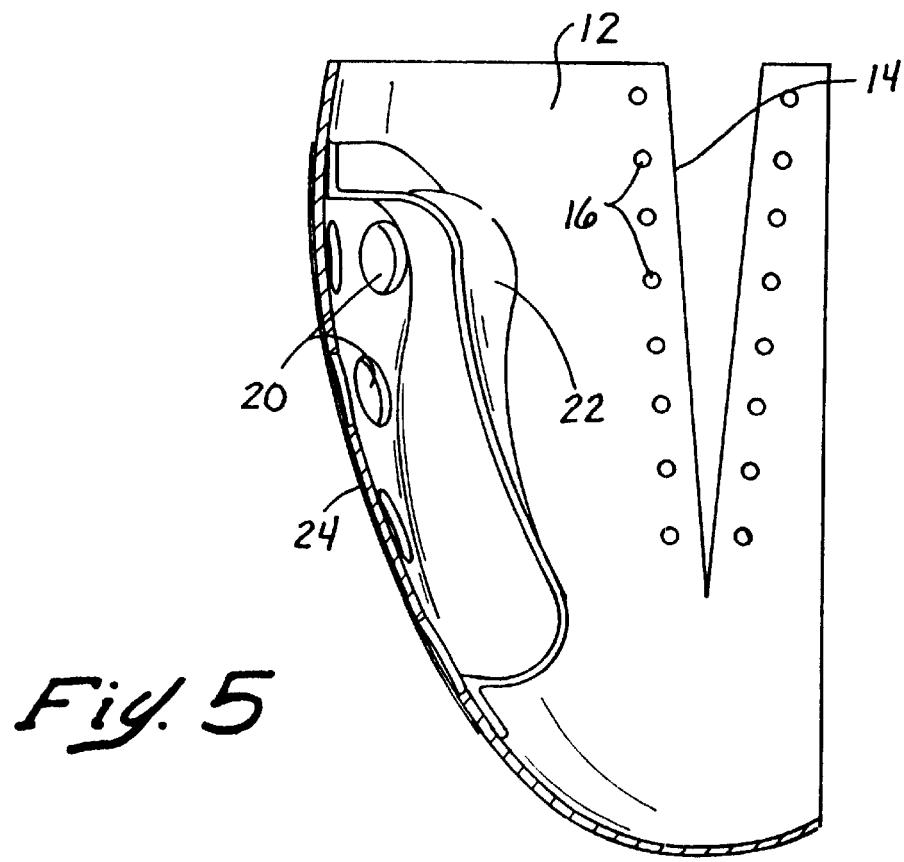
FIG. 5 is a cross-sectional view of a portion of the device illustrated in FIGS. 1 and 2, wherein the inflation pocket which forms a part of the invention is in an inflated state.
Figure 7:
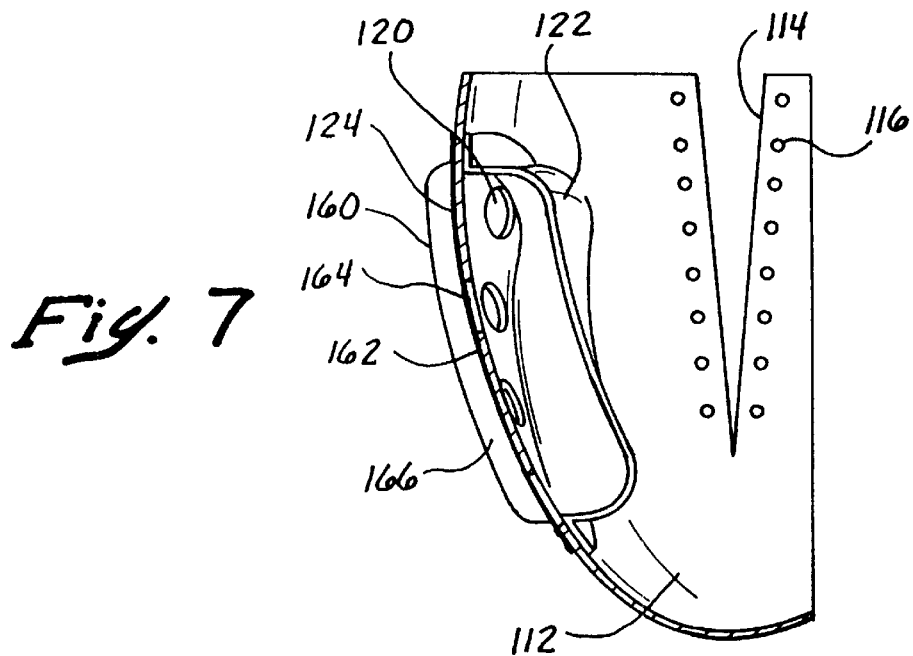
FIG. 7 is a cross-sectional view similar to FIG. 6, illustrating a portion of the device shown in FIGS. 3 and 4, wherein the inflation pocket and secondary recoil balloon are in a filled state.
Figure 10A:
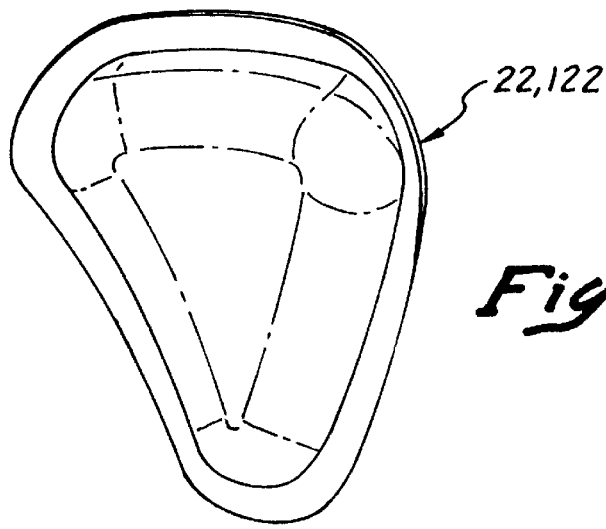
FIGS. 10A and 10B are plan views, in isolation, of the inflation pockets which form a part of the inventive device.
Figure 10B:
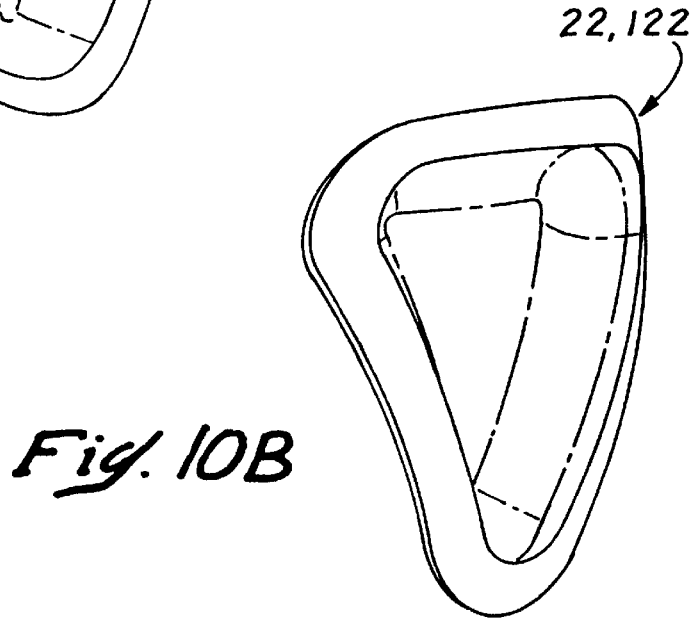

When the device 10, 110, 310 is first placed on the heart, the inflation pockets 22, 122, 322 are empty and completely collapsed. The device is actuated by introducing fluid into the inflation pockets. In the FIG. 12 embodiment, this is accomplished by the employment of a pressure monitoring syringe filled with saline or another suitable fluid. A needle is attached to the syringe and then inserted through the patient's skin 27 and into the septum 28, 128, 128', 328 of the fluid access port 26, 126, 126', 326 and the fluid is injected. The injected fluid fills the fluid access port, the inflation delivery line 30, 130, 130', 330', flows through the recoil balloons 24, 124, 324, and finally enters the inflation pockets 22, 122, 322. The pressure of the inflation pockets is monitored by a pressure wave, which occurs as the ventricle empties and refills. The fluid level is increased in the pockets until there is always a positive pressure present. This indicates that the inflation pockets 22, 122, 322 are in contact with the ventricle when it is systolic. FIGS. 5 and 7 illustrate each of the first and second disclosed embodiments wherein the inflation pockets 22 and 122, respectively, are in their filled state.

In the third embodiment, shown in FIG. 13, pressurized fluid will initially be introduced into the system from the pressurized fluid reservoir 280, through the one-way valve 282, rather than manually via a syringe. In all other respects, operation of the third embodiment is substantially similar to that described above with respect to the first, second, and fourth embodiments, and, in fact, any of the first, second, and fourth embodiments can utilize an automated fluid pressurization system as shown in the third embodiment.

Figure 6:
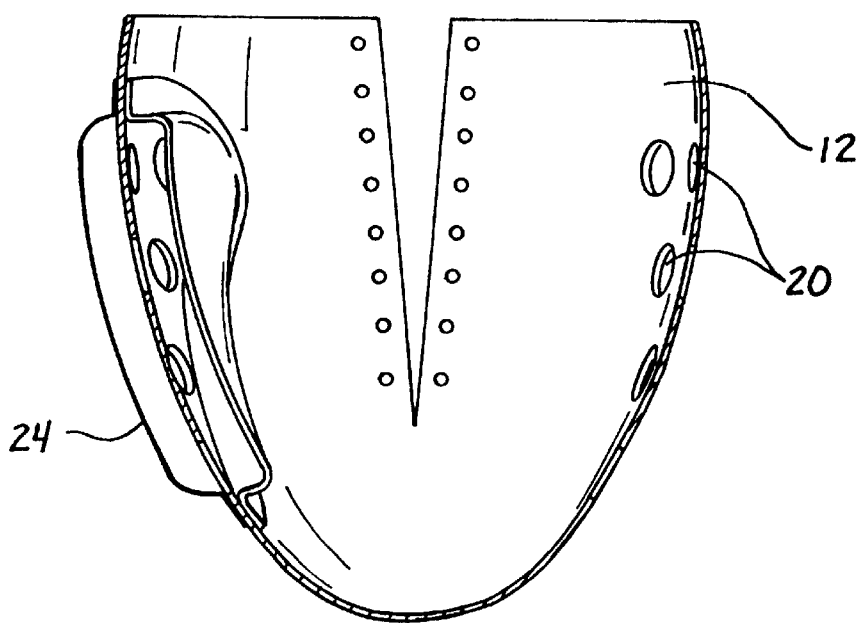
FIG. 6 is a cross-sectional view similar to FIG. 5, illustrating a portion of the device shown in FIGS. 1 and 2, during the fluid exchange phase.
Figure 8:
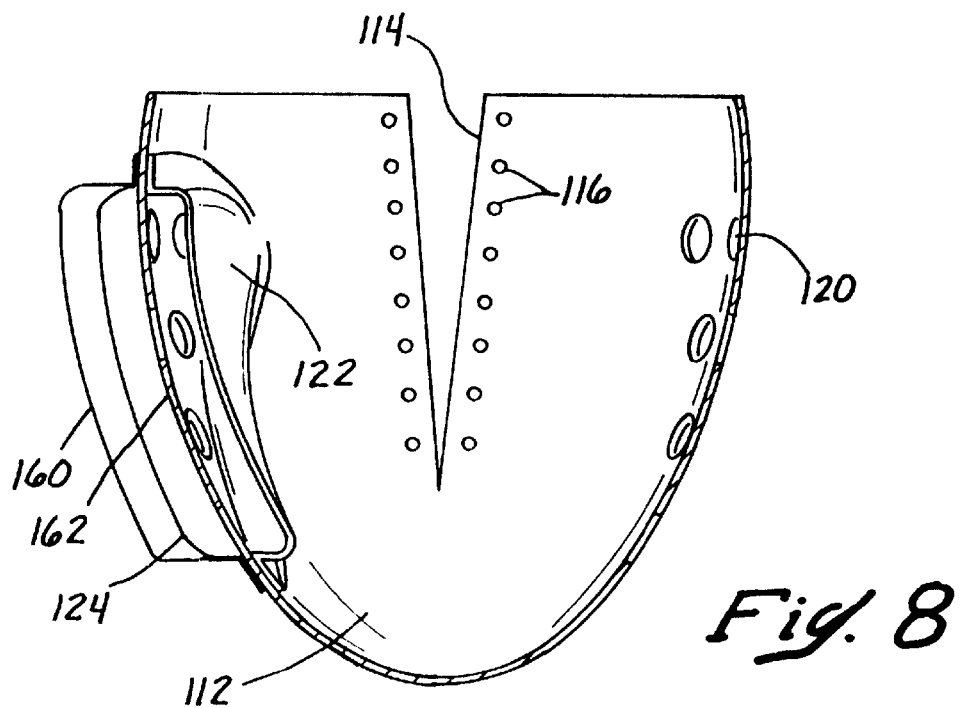
FIG. 8 is a cross-sectional view similar to FIG. 7, illustrating a portion of the device shown in FIGS. 3 and 4, during the fluid exchange phase.
Figure 9:
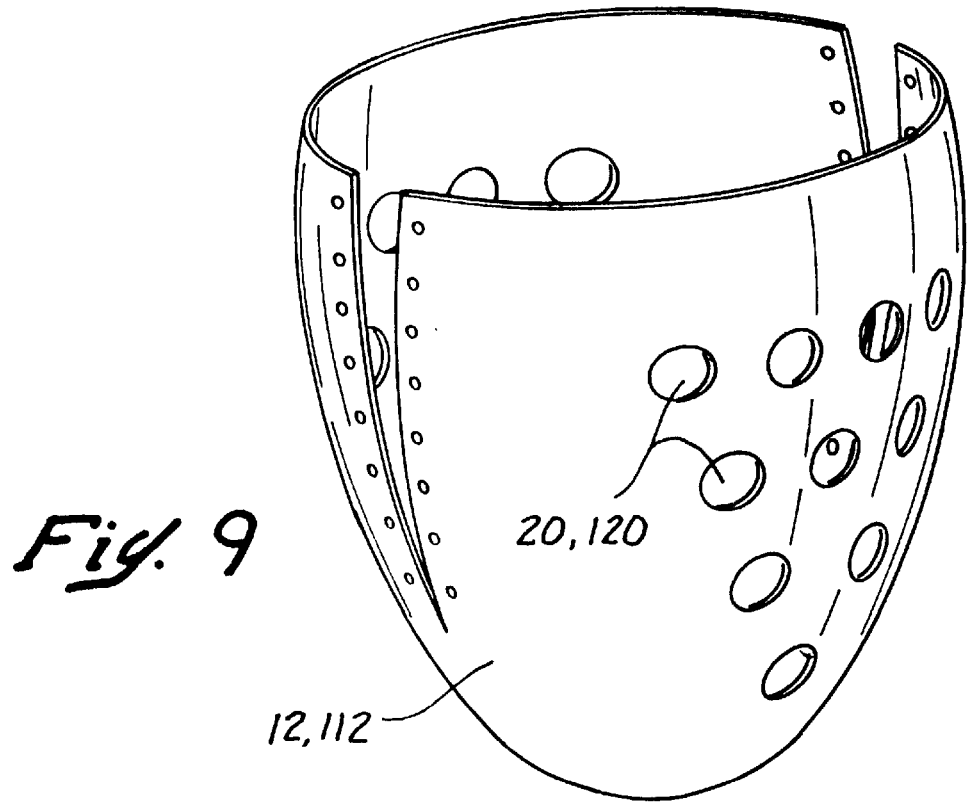
FIG. 9 is a perspective view of the containment structure which forms a part of the inventive device.

Once the device 10, 110, 310 has been initiated, or activated, it functions by assisting the failing and dilating heart muscle. The device provides a substantially constant external restraining force, which increases as the ventricle goes from a systolic to a diastolic state. As a ventricle is filled, it dilates and compresses its adjacent inflation pockets 22, 122, 322. This, in turn, reduces the volume of the inflation pockets. This is because, in the first two embodiments, the fluid is permitted to escape through the port holes 20, 120 in the frame 12, 112 into the recoil balloon 24, 124 on the external surface of the frame 12, 112, as shown in FIGS. 6 and 8, respectively. The fourth embodiment operates a little differently, because the recoil balloons 324 are disposed remotely from the containment structure 312, in the fluid lines 330. In this embodiment, as the fluid pressure increases, the fluid is displaced from the inflation pockets and is permitted to escape in a backwards direction through the fluid tubes 386 into the fluid line 330, which leads to the recoil balloon 324. As the volume of the inflation pockets decreases, the volume of the recoil balloon increases by an equal amount.

In any event, in all of the embodiments, in order for the fluid to enter the recoil balloons, the volume of the recoil balloons must increase. Thus, the wall of the balloons 24, 124, 324 must be forced to stretch and dilate. The force required to dilate these balloons increases as the volume increases, which in turn places a larger restraining force on the heart. Once the ventricle has completely dilated, the process is reversed and the potential energy now stored in the recoil balloons assists in forcing blood from the ventricle during the systolic state.

Over the course of time, as the patient responds to the action of the inventive device and the heart shrinks in size, the inflation pockets 22, 122, 322 will no longer be assisting the ventricle through the full operating cycle. This condition can be easily corrected by repeating the set-up procedure and observing the pressure wave. If a reduction of the size of the heart has occurred, the pressure wave will not be constant and, by simply adding additional fluid to the inflation pockets 22, 122, 322 via the fluid access ports 26, 126, 326, the inner boundary size of the device will shrink and it can again be made to assist the heart through its full operating cycle.

Again, it should be noted, as discussed supra, that the third embodiment illustrated in FIG. 13 offers a means for accomplishing the foregoing re-sizing process automatically. By using this embodiment, the practitioner can leave the patient for longer durations without making pressure volume adjustments to the inflation pockets 22, 122, 322. In this configuration, fluid is automatically added to the inflation pockets whenever a predetermined pressure low occurs, and is therefore self-adjusting until the reservoir is emptied.

The second disclosed embodiment offers a particular benefit in that if the practitioner determines that a patient would benefit from the application of a higher restraining force, such can be done by introducing additional fluid into the second fluid cavity 166 between the first and second recoil balloons, via the additional available fluid access port. Fluid forced into this space 166 will stretch the surface of the balloon 160, as illustrated in FIG. 7, thereby creating a greater resistance to the filling of the inner recoil balloon 124, which in turn increases the restraining force placed upon the heart. This adjustment may be made to any or all recoil balloons, as desired.

A major advantage of this design is that if a patient has an adverse reaction to the restraining forces of the frame 12, 112, 312 immediate relief may be obtained by removing fluid from the inflation pockets via the fluid access ports 26, 126, 126', 326.

It should be noted, as another advantageous feature of the invention, that the inflation pockets disclosed in any of the foregoing embodiments may be coated, if desired, with a drug infused osmosis material. If this is the case, the drug may leach out slowly for a term immediately after placement of the inventive device over a patient's heart, thereby aiding recovery.

Figure 17:
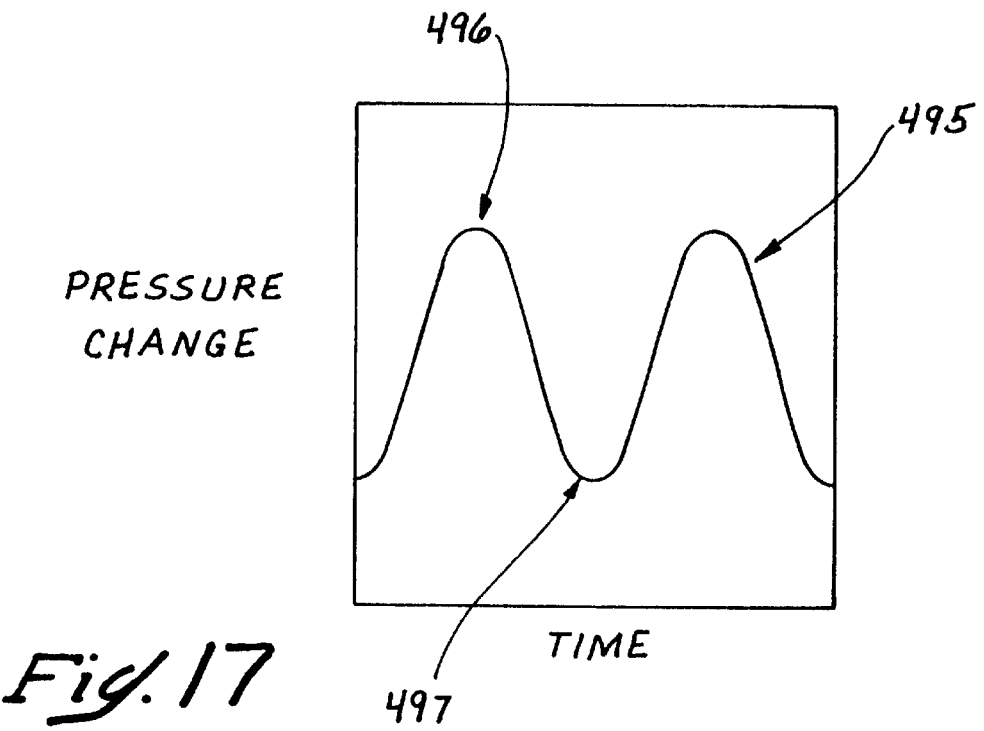
FIG. 17 is a conceptual graphical plot of the cyclical pressure measured by an external pressure monitor for the device illustrated in FIG. 14 when it is installed on a heart and working full time (i.e. in contact with the heart full time)
Figure 18:
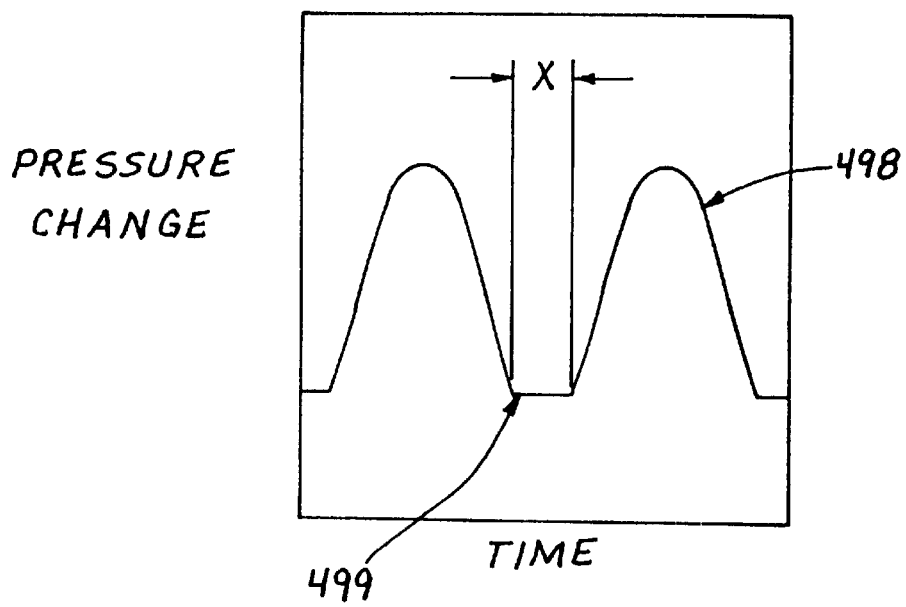
FIG. 18 is a conceptual graphical plot similar to that of FIG. 17 of the cyclical pressure measured by an external pressure monitor for the device illustrated in FIG. 14 when it is installed on a heart but not in contact with the external surface of the heart full time (i.e. it needs to be re-sized by addition of fluid)

Referring now, in particular, to FIGS. 17–19, there is illustrated a minimally invasive arrangement for monitoring and accurately measuring diastolic and systolic pressures and performance in an entirely new way. This data can be used for diagnostic purposes, to optimize the adjustment of the device, and/or to monitor therapy. In order to achieve this, the fluid access port 26, 126, 326 of the device 10, 110, 310 is directly attached, via a connecting flow line 492, to an external pressure monitoring system 493 (FIG. 19). This system may comprise a monitor, or a pulsating pump. To create a closed loop, a needle 494 is placed into the elastomeric septum 28, 128, 328, which, in turn, is attached to the connecting flow line 492 using, for example, a Luer lock connector 494a. Under normal operating conditions, diastolic expansion will cause the pressure inside the device to increase, and systolic contraction will cause the pressure to decrease. This pressure change occurs along the entire fluid path between the device and the pressure monitoring system, so that the monitoring system 493 receives data that translates into a complete pressure wave, as illustrated in FIGS. 17 and 18, which each represent generalized plots of pressure change over time. In FIG. 17, which represents a situation where the device is working full time, the data plots a full pressure SIN wave 495, with a peak diastolic pressure 496 and a minimum systolic pressure 497. On the other hand, as illustrated in FIG. 18, if the device is only in contact with a ventricle for a portion of the cardiac cycle, the pressure only changes while a compressive force between the device and the ventricle is in effect. This results in a partial pressure wave 498, with a flat spot 499 which represents the period of time x during which the device is not in contact with the ventricle, and thus is doing no work. In such an instance, the practitioner, viewing the plot on the monitoring device 493, would recognize the need to add fluid to resize the device to optimize its fit, as described supra, in order to ensure that it is working full time.

Although the inventive device has been disclosed as primarily having utility as a passive heart restraining or constraining device, it is within the scope of this invention to also provide direct active assistance to the heart if cardiac dysfunction occurs. This may happen immediately after installation of the device or at any time thereafter. In this mode of use, the device is used to provide systolic assistance instead of diastolic restraint. In order to achieve this, the fluid access ports of the device are directly attached to an external pump monitoring system 493, as illustrated in FIG. 19, for the purpose of controlling systolic inflation of the inflation pockets 322 by means of counter pressure pulsation. To create a closed loop control between the device and the pump/monitoring system 493, a needle 494 is placed into and attached to each fluid access port, which in turn is attached to an independent flow line 492 which is connected to the pump/monitoring system. Due to the rapid pulse rate required to achieve success with this procedure, it is preferred to use a low inertia medium, such as helium, as the fluid for activating the device 310.

While this invention has been described with respect to various specific examples and embodiments, it is to be understood that the invention is not limited thereto and that it can be variously practiced within the scope of the following claims. For example, while the foregoing embodiments are disclosed as being adapted for restraining both ventricles of the heart, it is clearly within the scope of this invention to install the device 10, 110, 310 in such a manner that only one ventricle is restrained. Typically, this one ventricle will be the left ventricle, as this is the one which typically causes the cardiomyopathy condition.

What is claimed is:

1. A passive device for treating a heart disorder, comprising:
   a first structure adapted to be placed over a patient's heart;
   a second structure adapted to apply pressure against a first portion of said heart during a portion of the pumping cycle of said heart; and
   a third structure adapted to apply pressure against a second portion of said heart during a portion of the pumping cycle of said heart;
   wherein the pressure applied by said second and third structures is independently controlled so that different pressures are selectively applied against said first and second heart portions, said second and third structures each comprising selectively closed systems which are actuated to operate during said patient's heart's pumping cycle solely by pumping action of the patient's heart.

2. The device as recited in claim 1, wherein said first structure comprises a containment structure adapted to enclose a substantial portion of said heart.

3. The device as recited in claim 2, wherein the containment structure is comprised substantially entirely of a flexible, biocompatible open mesh material, having a plurality of access openings disposed therein which are distributed about an outer surface of said containment structure.

4. The device as recited in claim 1, wherein said second structure comprises a first inflation pocket.

5. The device as recited in claim 4, wherein said first inflation pocket comprises a plurality of relatively small, spaced inflation pockets.

6. The device as recited in claim 4, wherein said third structure comprises a second inflation pocket disposed in a spaced relationship from said first inflation pocket.

7. The device as recited in claim 6, and further comprising a fluid injection port for injecting fluid into each of said first and second inflation pockets, wherein differing amounts of fluid are injected into each of the inflation pockets independently, thereby permitting different pressures to be selectively applied against said first and second heart portions.

8. A device for treating a heart disorder, comprising:
   a first structure adapted to be placed over a patient's heart;
   a second structure, comprising an inflation pocket adapted to apply pressure against a first portion of said heart during a portion of the pumping cycle of said heart;
   a recoil balloon disposed outwardly of said inflation pocket and a fluid passage disposed between said inflation pocket and said recoil balloon to permit fluid to be exchanged therebetween; and
   a third structure adapted to apply pressure against a second portion of said heart during a portion of the pumping cycle of said heart;
   wherein the pressure applied by said second and third structures is independently controlled so that different pressures are selectively applied against said first and second heart portions.

9. The device as recited in claim 8, wherein said inflation pocket is filled with fluid, and said first portion of said heart is the left ventricle, wherein when the heart enters a diastolic state, the left ventricle expands against said inflation pocket, thereby forcing fluid from said inflation pocket through said fluid passage and into said recoil balloon.

10. The device as recited in claim 9, wherein when said heart enters a systolic state, said fluid returns through said fluid passage from the recoil balloon into the inflation pocket, so that the inflation pocket becomes pressurized and exerts pressure against said left ventricle.

11. A device for treating a heart disorder, comprising:
   a first structure adapted to be placed over a patient's heart;
   a first inflation pocket adapted to apply pressure against a first portion of said heart during a portion of the pumping cycle of said heart; and
   a second inflation pocket disposed in spaced relationship from said first inflation pocket and being adapted To apply pressure against a second portion of said heart during a portion of the pumping cycle of said heart;
   a fluid injection port for injecting fluid into each of said first and second inflation pockets, wherein differing amounts of fluid are injected into each of the inflation pockets independently, thereby permitting different pressures to be selectively applied against said first and second heart portions;
   said fluid injection port comprising two sepia disposed just beneath the skin of said patient, each of which is fluidly connected through a separate fluid passage to a corresponding one of said inflation pockets.

12. A device for treating a heart disorder, comprising:
   a first structure adapted to be placed over a patient's heart;
   a first inflation pocket adapted To apply pressure against a first portion of said heart during a portion of the pumping cycle of said heart, and a second inflation pocket disposed in spaced relationship from said first inflation pocket and being adapted to apply pressure against a second portion of said heart during a portion of the pumping cycle of said heart;

a fluid injection port for injecting fluid into each of said first and second inflation pockets, wherein differing amounts of fluid are injected into each of the inflation pockets independently, thereby permitting different pressures to be selectively applied against said first and second heart portions;

said fluid injection port comprising a pressurized fluid reservoir and a one-way valve, so that fluid may be automatically injected into each of the first and second inflation pockets independently, responsive to pressure in each pocket.

13. A device for treating a heart disorder, comprising:

a first structure adapted to be placed over a patient's heart;

a second structure disposed within said first structure adapted to support a portion of said heart during at least a period of time when the heart is in a diastolic state; and a third structure disposed outside of said first structure which is adapted to operate in conjunction with the second structure to support the heart.

14. The device as recited in claim 13, wherein said first structure comprises a containment structure adapted to enclose a substantial portion of said heart.

15. The device as recited in claim 14, wherein said third structure is spaced from said first structure.

16. The device as recited in claim 14, and further comprising a drug delivery line for selectively delivering drugs to said heart through said first structure.

17. The device as recited in claim 13, wherein said second structure comprises an inflation pocket comprised of a substantially non-elastic biocompatible material.

18. The device as recited in claim 14, wherein said third structure comprises a recoil balloon.

19. The device as recited in claim 18, and further comprising a fluid passage disposed between said inflation pocket and said recoil balloon to permit fluid to be exchanged therebetween.

20. The device as recited in claim 19, and further comprising a fluid injection port for injecting fluid into said inflation pocket, wherein the amount of fluid being injected into said inflation pocket is increased responsive to the size of the heart, in order to ensure that pressure is applied by said inflation pocket against said heart at least when said heart is in a diastolic state.

21. A device for treating a heart disorder, comprising:

a containment structure adapted for placement over a patient's heart;

a first inflation pocket adapted to apply pressure against the left heart ventricle during at least a period of time when the heart is in a diastolic state;

a second inflation pocket adapted to apply pressure against the right heart ventricle during at least a period of time when the heart is in a diastolic state; and a fluid injection port comprising a fluid line for independently delivering pressurized fluid to each of said first and second inflation pockets, so that different pressures are selectively applied against each of said left and right heart ventricles; wherein no active heart assist unit is connected to said fluid injection port, and the pumping action of the patient's heart actuates each of the first and second inflation pockets to selectively apply pressure against the heart daring the heart pumping cycle.

22. A device for treating a heart disorder, comprising:

a containment structure adapted for placement over a patient's heart;

an inflation pocket disposed within said containment structure and being adapted to support a portion of the heart during at least a period of time when the heart is in a diastolic state; and a recoil balloon disposed outwardly of said containment structure which is adapted to operate in conjunction with said inflation pocket to support the heart.

23. A method for treating a heart disorder, comprising the steps of:

placing a containment structure over a patient's hear;

inflating a first inflation pocket which is disposed to lie adjacent to said first heart portion within said containment structure to a first level of pressure, which is then applied against a first portion of the patient's heart;

inflating a second inflation pocket which is disposed to lie adjacent to said second heart portion within said containment structure to a second level of pressure, which is then applied against a second portion of said heart; and closing each of said first and second inflation pockets to further inflow or outflow of fluid, so that cyclical beating of said heart causes said pockets to cyclically act against said heart without assistance from active heart assist devices.

24. A device for Treating a heart disorder, comprising:

a containment structure adapted to be placed over a patient's heart; and a plurality of inflation pockets adopted to apply pressure against a portion of said heart during at least a portion of the pumping cycle of said hear;

wherein said plurality of inflation pockets comprise a plurality of inflation pockets which are each substantially smaller than a ventricle of said heart, and which are spaced with respect to one another, said plurality of inflation pockets together being adapted to apply sufficient force to restrain a heart ventricle, without assistance of any active heart assist device.

25. The device as recited in claim 24, wherein said containment structure has an outer surface and comprises an open mesh material having a plurality of openings distributed about said outer surface, said plurality of openings providing access for visualizing coronary arteries and performing bypass procedures on said heart without removing said device.

26. The device as recited in claim 24, and further comprising a fluid injection port and a fluid passage connected between said fluid injection port and each of said plurality of inflation pockets, for injecting fluid into each of said plurality of inflation pockets.

27. A device for treating a heart disorder, comprising:

a containment structure adapted to be placed over a patient's heart; and a plurality of inflation pockets adapted to apply pressure against a portion of said heart during at least a portion of the pumping cycle of said heart;

a fluid injection port and a fluid passage connected between said fluid injection port and each of said plurality of inflation pockets, for injecting fluid into each of said plurality of inflation pockets; and a recoil balloon which is fluidly connected to each of said plurality of inflation pockets, said recoil balloon receiving fluid from said inflation pockets during a portion of the heart pumping cycle and delivering fluid To said inflation pockets during another portion of the heart pumping cycle;

wherein said plurality of inflation pockets comprise a plurality of inflation pockets which are each substantially smaller than a ventricle of said heart, and which are spaced with respect to one another, said plurality of inflation pockets together being adapted to apply sufficient force to restrain a heart ventricle.

28. The device as recited in claim 27, wherein said recoil balloon is disposed at a location remote from said containment structure.

29. The device as recited in claim 28, wherein said recoil balloon is disposed in said fluid passage, said fluid passage comprising a fluid line, said recoil balloon being connected to said fluid line using detachable fittings so that it is readily replaceable.

30. A device for treating a heart disorder, comprising:
- a containment structure adapted to be placed over a patient's heart;
- a drug injection port;
- a drug delivery line fluidly connected to said drug injection port, said drug delivery line including a distal portion which is disposed about a circumferential portion of said containment structure; and
- a plurality of drug flow holes spaced along said drug delivery line distal portion, for selectively supplying drugs to said heart.

* * * * *